US011963802B2

(12) United States Patent
Sato et al.

(10) Patent No.: US 11,963,802 B2
(45) Date of Patent: Apr. 23, 2024

(54) DISEASE ONSET RISK PREDICTION DEVICE, METHOD, AND NON-FUGITIVE RECORDING MEDIUM FOR STORING PROGRAM

(71) Applicant: OMRON HEALTHCARE Co., Ltd., Kyoto (JP)

(72) Inventors: Hironori Sato, Kyoto (JP); Mitsuharu Konishi, Kyoto (JP); Seisuke Fujiwara, Kyoto (JP); Daisuke Nozaki, Kyoto (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 979 days.

(21) Appl. No.: 16/906,300

(22) Filed: Jun. 19, 2020

(65) Prior Publication Data

US 2020/0315548 A1    Oct. 8, 2020

Related U.S. Application Data

(63) Continuation of application No. PCT/JP2018/046240, filed on Dec. 17, 2018.

(30) Foreign Application Priority Data

Dec. 27, 2017  (JP) ................. 2017-252655

(51) Int. Cl.
    *A61B 5/00*      (2006.01)
    *A61B 5/021*     (2006.01)
(52) U.S. Cl.
    CPC ........ *A61B 5/7275* (2013.01); *A61B 5/02125* (2013.01); *A61B 5/4806* (2013.01); *A61B 5/7246* (2013.01)

(58) Field of Classification Search
    CPC . A61B 5/7275; A61B 5/02125; A61B 5/4806; A61B 5/7246
    See application file for complete search history.

(56) References Cited

U.S. PATENT DOCUMENTS

2005/0113650 A1*  5/2005  Pacione .............. A61B 5/4866
                                                        600/300
2008/0114219 A1   5/2008  Zhang et al.
(Continued)

FOREIGN PATENT DOCUMENTS

JP    2007-86906 A    4/2007
JP    2017-131495 A   8/2017
(Continued)

OTHER PUBLICATIONS

International Preliminary Report on Patentability (Chapter II) of the International Preliminary Examining Authority for PCT/JP2018/046240 with search date of Aug. 2, 2019.
(Continued)

*Primary Examiner* — Jonathan T Kuo
(74) *Attorney, Agent, or Firm* — Wenderoth, Lind & Ponack, L.L.P.

(57) ABSTRACT

Prediction of a disease onset risk is enabled by focusing on characteristic change in biological information depending on a time period. A prediction device SV acquires blood pressure data and determination data on irregular pulse waves and acquires input data indicating a sleep time period or information indicating a determination result of a sleep condition. Further, based on the input data indicating the sleep time period or the information indicating the determination result of the sleep condition, the sleep time period is set as a prediction target period and is divided into a first half and a second half. A degree of change in the blood pressure data and a degree of change in frequency of occurrence of irregular pulse waves in each of the first half time period and (Continued)

the second half time period are calculated and multiplied. With this, a total risk in the sleep time period is calculated. Further, by comparing the total risk with a determination threshold, whether an onset risk for cardiovascular and cerebrovascular diseases is high or low is determined.

16 Claims, 10 Drawing Sheets

(56) References Cited

U.S. PATENT DOCUMENTS

| | | | | |
|---|---|---|---|---|
| 2017/0277858 A1* | 9/2017 | Okubo | ............... | G16H 50/20 |
| 2018/0078199 A1* | 3/2018 | Sankari | ............ | A61B 5/316 |

FOREIGN PATENT DOCUMENTS

| | | |
|---|---|---|
| WO | 2008/054580 A2 | 5/2008 |
| WO | 2016/043299 A1 | 3/2016 |

OTHER PUBLICATIONS

English translation of International Preliminary Report on Patentability (Chapter II) of the International Preliminary Examining Authority for PCT/JP2018/046240 with search date of Aug. 2, 2019.
International Preliminary Report on Patentability dated Jul. 2, 2020 in International (PCT) Patent Application No. PCT/JP2018/046240.
International Search Report of the International Searching Authority for PCT/JP2018/046240 dated Mar. 5, 2019.
English translation of International Search Report of the International Searching Authority for PCT/JP2018/046240 dated Mar. 5, 2019.

* cited by examiner

PULSE WAVE DATA

FREQUENCY ANALYSIS OF HEARTBEAT INTERVAL FLUCTUATION

AUTONOMIC NERVE BALANCE

SLEEP CONDITION

DISEASE ONSET RISK PREDICTION DEVICE, METHOD, AND NON-FUGITIVE RECORDING MEDIUM FOR STORING PROGRAM

CROSS-REFERENCE TO RELATED APPLICATIONS

This is a continuation of International Application 2017-252655, with an international filing date of Dec. 27, 2017, and International Application PCT/JP2018/046240, with an international filing date of Dec. 17, 2018 filed by applicant, the disclosure of which is hereby incorporated by reference in its entirety.

Technical Field

An embodiment of the present invention relates to a disease onset risk prediction device, a method, and a non-fugitive recording medium for storing a program, which are used for predicting an onset risk for cardiovascular and cerebrovascular diseases, for example.

BACKGROUND ART

In general, hypertension causes no subjective symptoms in many cases. Even when there are symptoms, one can only be aware of relatively mild symptoms such as a headache and heavy-headedness in many cases. However, when hypertension is left untreated, a risk of suddenly developing serious diseases such as cerebral apoplexy and myocardial infarction is high, which is terribly unfavorable. In view of this, there has been proposed a technology of measuring blood pressure regularly and predicting an onset risk for the serious diseases described above, based on change in the measured blood pressure values (for example, see JP 2007-86906 A).

SUMMARY OF INVENTION

Biological information such as blood pressure and an electrocardiogram not only changes by being influenced by external factors such as weather, excitement, and stress, but also changes uniquely depending on a time period.

For example, types of hypertension include: office hypertension where blood pressure is normal in a time period of staying at home but rises in a time period of working at an office; and masked hypertension where blood pressure is normal during the daytime but rises during the nighttime. Further, types of masked hypertension include early-morning hypertension where blood pressure abruptly rises only in a time period for approximately one to two hours after and before rising. Early-morning hypertension is a steep blood pressure rise before arousal caused by high vascular constriction in relation to acceleration of sympathetic nerve activity, which is decelerated during sleep, and simultaneously in relation to acceleration of adrenocorticotropic hormones (ACTH). Particularly, early-morning hypertension has been significantly associated with serious cardiovascular and cerebrovascular diseases such as cerebral apoplexy and myocardial infarction that are developed in the early morning or in the morning.

However, the technology described in Patent Document 1 is for predicting change in human blood pressure based on external conditions such as weather and for informing him/her that an onset risk for circulatory system diseases is high when a rise in blood pressure is predicted. Thus, an onset risk for diseases that are associated with change in biological information not particularly depending external conditions but depending on a time period cannot be predicted.

In order to solve the above-mentioned problem, an aspect of the present invention has an object to provide a disease onset risk prediction device, a method, and a non-fugitive recording medium for storing a program, which enable prediction of a disease onset risk by focusing on characteristic change in biological information depending on a time period.

In order to achieve the above-mentioned object, a disease onset risk prediction device, a method, or a non-fugitive recording medium for storing a program according to a first aspect of the present invention acquires biological information of a user, which is measured by a measurement unit, divides a prediction target period set in advance into a plurality of time periods, generates information indicating change in the biological information in the plurality of time periods, and predicts an onset risk for a specified disease for the user by comparing the information indicating the change with criteria set in advance in accordance with the specified disease.

According to the first aspect of the present invention, the prediction target period is divided into the plurality of time periods, and the change in the biological information in the plurality of divided time periods is compared with the criteria. With this, an onset risk prediction result for the specified disease can be obtained. Thus, the characteristic change in the biological information depending on the time period can be detected relatively easily, and an onset risk for the specified disease can be predicted based on the detection result of the characteristic change.

According to a second aspect of the present invention, in the first aspect, blood pressure information is acquired as the biological information, information indicating change in the acquired blood pressure information in the plurality of time periods is generated, and an onset risk for the specified disease for the user is predicted by comparing the information indicating the change in the blood pressure information with criteria set in advance in accordance with the specified disease.

According to the second aspect of the present invention, an onset risk for the specified disease is predicted by comparing change in blood pressure information in the plurality of divided time periods with the criteria. Thus, the characteristic change in the blood pressure depending on the time period can be detected relatively easily, and an onset risk for the specified disease can be predicted based on the detection result of the characteristic change.

According to a third aspect of the present invention, in the first aspect, blood pressure information and information indicating occurrence condition of irregular pulse waves are acquired as the biological information, first change information indicating change in the acquired blood pressure information in the plurality of time periods is generated, and second change information indicating change in the occurrence condition of the irregular pulse waves in the plurality of time periods is generated. Further, the first change information and the second change information are weighted and synthesized, and the third change information indicating such a synthetic result is compared with the criteria set in advance in accordance with the specified disease. In this manner, an onset risk for the specified disease for the user is predicted.

According to the third aspect of the present invention, both the blood pressure information and the information indicating occurrence condition of irregular pulse waves are used as the biological information, the change in the blood pressure information in the plurality of divided time periods and the change in the occurrence condition of irregular pulse waves in the plurality of time periods are synthesized, and an onset risk for the specified disease is predicted by comparing the synthetic result with the criteria. Specifically, in consideration of the change in the occurrence condition of irregular pulse waves in addition to the change in blood pressure in the time periods, an onset risk for the specified disease is predicted. Thus, the onset risk for the specified disease can be predicted more accurately.

According to a fourth aspect of the present invention, in any of the first to third aspects, information indicating a sleep time period of the user, which is input with an input unit, is further acquired, the sleep time period of the user is set as the prediction target period based on the information indicating the sleep time period, and the sleep time period is divided into a plurality of time periods.

According to the fourth aspect of the present invention, for example, when the user inputs information indicating his or her own sleep time period with an own terminal, the information indicating the sleep time period is acquired from the terminal. Further, based on the acquired input information, the sleep time period is set as the prediction target period, and the sleep time period is divided into the plurality of time periods. Thus, the characteristic change in the biological information depending on the time period, which is caused in the sleep time period of the user, can be detected, and an onset risk for the specified disease can be predicted based on the characteristic change in the biological information depending on the time period.

According to a fifth aspect of the present invention, in any of the first to third aspects, information indicating a sleep condition of the user, which is obtained by a measurement unit, is acquired, a sleep time period of the user is estimated based on the information indicating the sleep condition, and the sleep time period is set as the prediction target period. Further, along with this, the division boundary point in the sleep time period is set based on the information indicating the sleep condition, and the sleep time period is divided into the plurality of time periods at the division boundary point.

According to the fifth aspect of the present invention, the actual sleep time period of the user is set as the prediction target period. Further, the sleep time period is divided into the plurality of time periods at the division boundary point set based on the contents of the sleep condition of the user. Thus, the characteristic change in the biological information in the actual sleep time period of the user, which depends on the time period, can be detected, an onset risk for the specified disease can be predicted based the characteristic change.

According to a sixth aspect of the present invention, in any of the first to fifth aspects, the generation unit calculates statistic values of the biological information, which are measured at a plurality of times in each of the plurality of time periods and generates information indicating change in the statistic values calculated in the plurality of time periods.

According to the sixth aspect of the present invention, when a plurality pieces of biological information are measured at times in the plurality of divided time periods, statistic values of the plurality pieces of the biological information are calculated in each time period, and an onset risk for the specified disease is predicted based on the change in the statistic values in the time periods. Therefore, an influence of fluctuation in the biological information can be reduced, and the characteristic change in the biological information depending on the time period can be detected at high accuracy. With this, accuracy of predicting an onset risk for the specified disease can be improved.

Thus, according to each aspect of the present invention, there can be provided the disease onset risk prediction device, the method, and the non-fugitive recording medium for storing the program that enable the prediction of the disease onset risk by focusing on the characteristic change in the biological information depending on the time period.

DESCRIPTION OF EMBODIMENTS

Now, with reference to the drawings, an embodiment of the present invention is described.

Application Example

First, an example of a case to which the present invention is applied is described.

Figure 1:
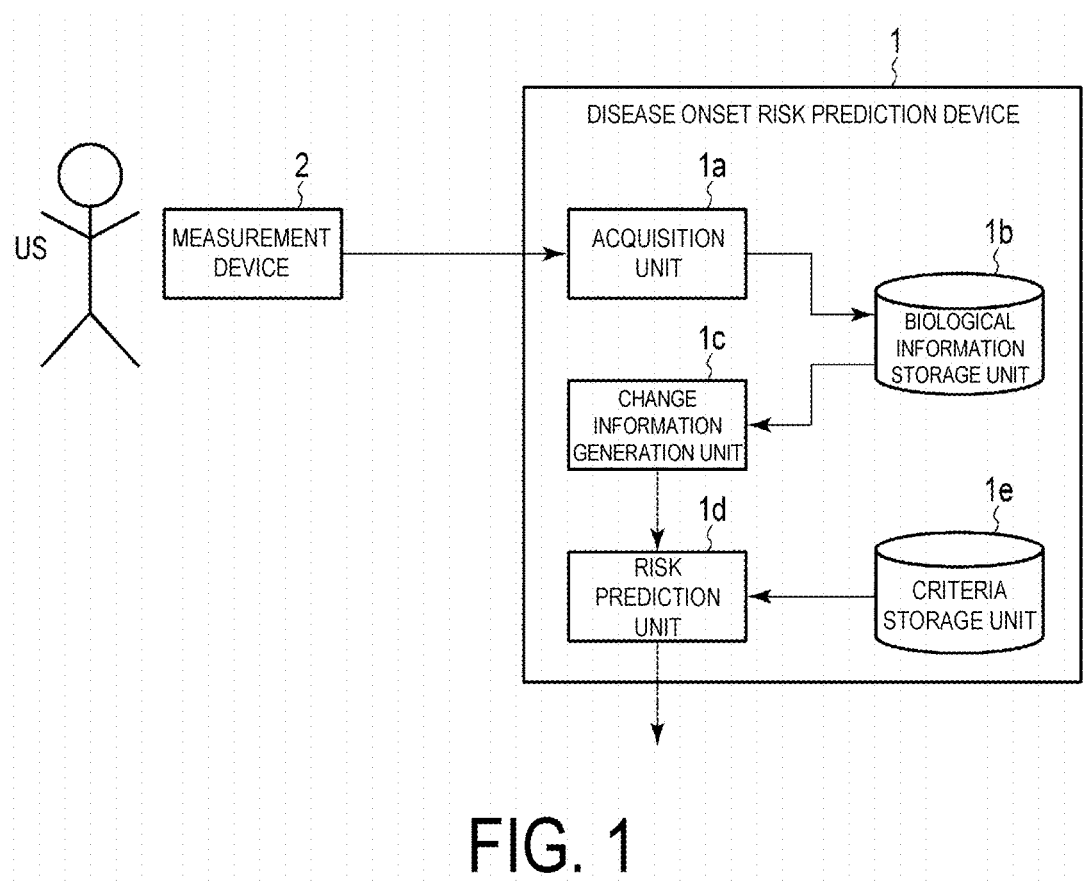
FIG. 1 is a block diagram illustrating an application example of a disease onset risk prediction device according to the present invention.

FIG. 1 schematically illustrates a configuration example of a disease onset risk predication device according to the application example. In FIG. 1, a user US wears a measurement device 2. The measurement device 2 is a wearable terminal, for example, and includes a biological information measurement unit and a wireless communication unit.

The biological information measurement unit includes a blood pressure measurement unit and a pulse wave measurement unit. The blood pressure measurement unit measures blood pressure values of the user US (including a systolic blood pressure and a diastolic blood pressure) and generates blood pressure data. The pulse wave measurement unit measures pulse waves of the user US. Further, based on the measurement timings of the measured pulse waves, it is determined whether the pulse waves are regular pulse waves or irregular pulse waves, and data indicating an occurrence condition of irregular pulse waves is generated. The operation of measuring blood pressure values and pulse waves may be performed in accordance with a measurement instruction operated by the user US or may be performed automatically at a time interval that is set in advance.

The wireless communication unit accumulates the biological information at a time or for a fixed time, the biological information including: the blood pressure data and the data indicating the occurrence condition of irregular pulse waves that are generated by the biological information measurement unit; and the measurement time thereof, and then transmits the biological information to a disease onset risk prediction device 1 via a wireless communication network.

As constituent elements according to the present invention, the disease onset risk prediction device 1 includes: an acquisition unit 1a, a biological information storage unit 1b, a change information generation unit 1c, a risk prediction unit 1d, and a criteria storage unit 1e.

The acquisition unit 1a receives the biological information transmitted from the measurement device 2 and stores the biological information in the biological information storage unit 1b. The change information generation unit 1c sets a sleep time period of the user US as, for example, a prediction target period and divides the sleep time period into two time periods including a first half and a second half, for example. For example, the user US inputs the sleep time period of the user US with a device such as a user terminal and the measurement device 2 having an input function, and the disease onset risk prediction device 1 acquires information indicating the sleep time period that is input. In this manner, the setting is performed.

Further, the change information generation unit 1c reads the biological information from the biological information storage unit 1b and subjects the read biological information to, for example, averaging processing in each of the first half and the second half time periods in the sleep time period. Further, a degree of change in the average values of the biological information between each of the time periods, which are acquired from the averaging processing, is obtained.

As one example, the biological information includes the blood pressure data and the data indicating the occurrence condition of irregular pulse waves. Thus, the change information generation unit 1c calculates an average value of each of the blood pressure data and the data indicating the occurrence condition of irregular pulse waves in each of the time periods of the first half and the second half and calculates a degree of change in the average values between each of the time periods. Specifically, a degree of change in blood pressure and a degree of change in frequency of occurrence of irregular pulse waves between the first half and the second half in the sleep time period are calculated.

Further, the degree of change in blood pressure and the degree of change in frequency of occurrence of irregular pulse waves that are calculated are multiplied by a weight coefficient and added to or multiplied by each other, and the calculation result is set as a score indicating a magnitude of change in the biological information between the first half and the second half in the sleep time period of the user US. The change score is provided to the risk prediction unit 1d as information for determining a disease onset risk.

The risk prediction unit 1d compares the change score, which is obtained by the change information generation unit 1c, with criteria stored in advance in the criteria storage unit 1e. Further, for example, when the change score exceeds the criteria, it is determined that a case of early-morning hypertension is suspected, for example. Further, when it is determined that the user US is a suspected case of early-morning hypertension, the risk prediction unit 1d generates a notification message for notifying the user that an onset risk for cardiovascular and cerebrovascular diseases is high. Further, for example, the notification message is transmitted to a terminal of the user US or a terminal of a family physician of the user US.

As described above, in the disease onset risk prediction device 1, the sleep time period is divided into the first half and the second half, the degree of change in the blood pressure data and the degree of change in frequency of occurrence of irregular pulse waves between the time periods are integrated to calculate the change score of the biological information, and the change score is compared with the criteria set in advance. In this manner, it is determined whether an onset risk for cardiovascular and cerebrovascular diseases is high or low. Therefore, an onset risk for cardiovascular and cerebrovascular diseases caused by early-morning hypertension can be determined with a relatively simple method, and a user or a family physician can take a prevention measure at an early stage or perform treatment as needed based on the determination result of the onset risk.

Embodiment (1) System

Figure 2:
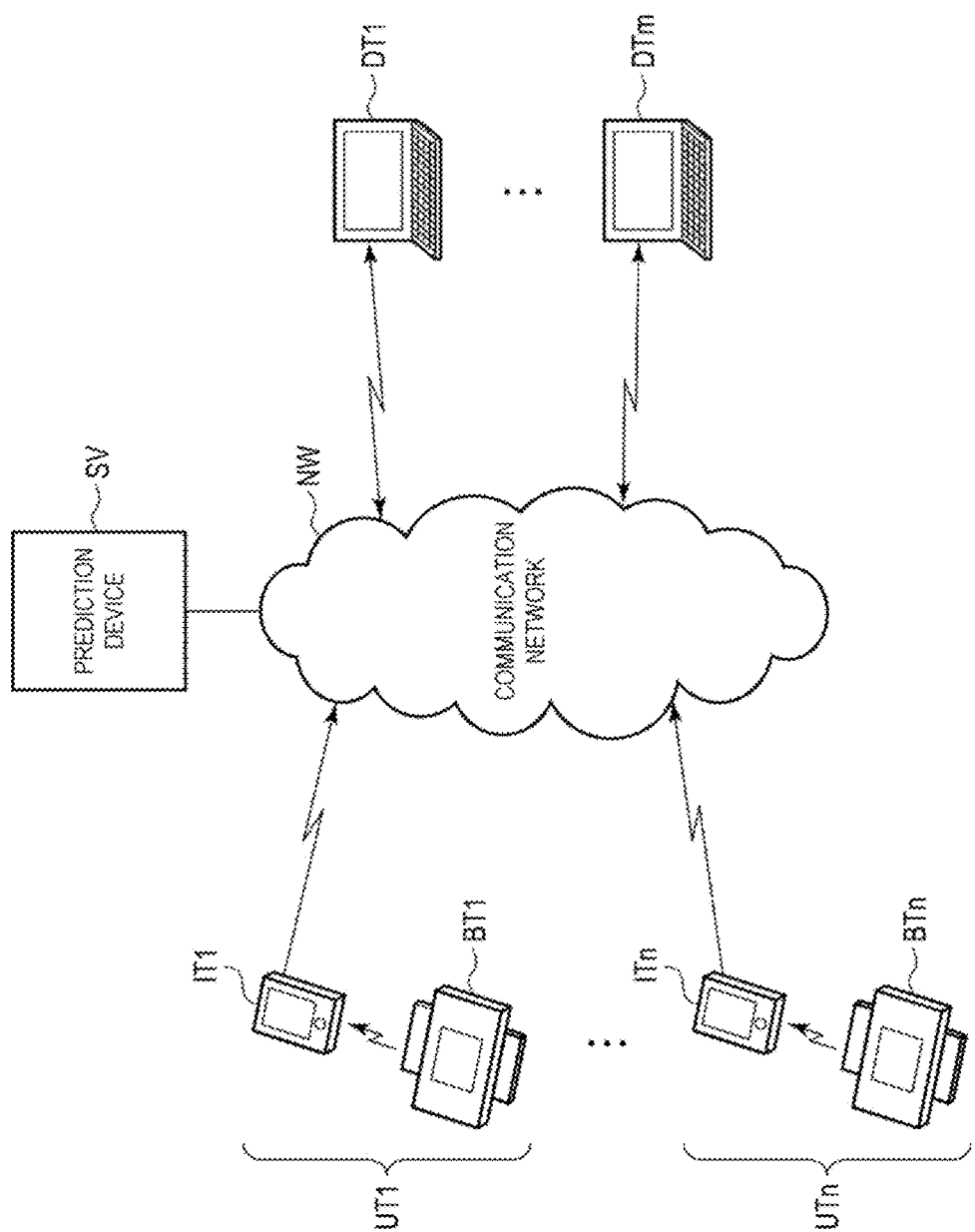
FIG. 2 is a diagram illustrating an overall configuration of a system including a disease onset risk prediction device according to the present invention.

FIG. 2 is a diagram illustrating one example of an overall configuration of a system including the disease onset risk prediction device 1 according to an embodiment of the present invention.

The system includes a disease onset risk prediction device (hereinafter referred to as a prediction device) SV, for example, on the Web or the cloud. Further, the prediction device SV and terminals used by users (hereinafter referred to as user terminals) UT1 to UTn and the prediction device SV and terminals used by medical personnel such as physicians (hereinafter referred to as doctor terminals) DT1 to DTm are communicable with each other via a communication network NW.

For example, the doctor terminals DT1 to DTm are fixed installation type personal computers, mobile notebook type personal computers, or tablet type terminals. Further, the doctor terminals DT1 to DTm each include at least a mailer and a browser. Further, when the mailer is used, a notification mail is received from the prediction device SV. When the browser is used, the prediction device SV can be accessed.

For example, the user terminals UT1 to UTn include wearable type measurement devices BT1 to BTn and information terminals IT1 to ITn. For example, each of the measurement devices BT1 to BTn is worn by a user on a wrist, measures blood pressure and pulse waves of the user by an operation by the user or at a timing or a time interval set in advance, and wirelessly transmits the blood pressure data and the pulse wave data that are acquired by measurement to each of the information terminals IT1 to ITn by a wireless interface. A measurement time and user identification information (user ID) are added to or inserted in the blood pressure data and the pulse wave data.

As a method of measuring blood pressure, for example, the oscillometric method is used. In place of this, the beat-by-beat method of measuring one heartbeat; and the trigger measurement method of measuring blood pressure at a spot while estimating blood pressure change by the pulse transit time (PTT) method and regarding the estimated change as a trigger may be used. Further, the type of the measurement devices BT1 to BTn is not limited to a wearable type to be worn on a wrist and may be a type worn on an upper arm and the like or an installation type. Further, the blood pressure monitor and the pulse wave monitor may be provided as separate devices, and the blood pressure data and the pulse wave data that are measured respectively by those devices may be transmitted to the information terminals IT1 to ITn.

For example, the information terminals IT1 to ITn are mobile information terminals such as smartphones and tablet type terminals or fixed installation type personal computers. The information terminals IT1 to ITn receive the blood pressure data and the pulse wave data transmitted from the measurement devices BT1 to BTn, and temporarily accumulate the data in a memory. Further, based on the pulse wave data, it is determined whether the pulse waves are regular pulse waves or irregular pulse waves from a deviation amount of the measurement timing of each pulse wave, and the regular/irregular determination data of the pulse waves (hereinafter referred to as pulse wave determination data) is stored in the memory. For example, the information terminals IT1 to ITn read the blood pressure data and the pulse wave determination data, which are accumulated in the memory, from the memory by the fixed number of data or for a fixed time, and transmit the data to the prediction device SV via the communication network NW.

Further, the information terminals IT1 to ITn transmit sleep information of users to the prediction device SV via the communication network NW. The sleep information includes information indicating a sleep time period. The users themselves may manually input information indicating a sleep time period with input units of the information terminals IT1 to ITn, or estimation may be made from the pulse wave data. Note that a method of estimating the sleep time period from the pulse wave data is described later.

Further, each of the information terminals IT1 to ITn includes the mailer and the browser, receives a message indicating a prediction result of an onset risk for cardiovascular and cerebrovascular diseases from the prediction device SV via any one of the mailer and the browser, and displays the received message on a display.

Note that, as the wireless interface used between the measurement devices BT1 to BTn and the information terminals IT1 to ITn, for example, a wireless interface that adopts a short range radio data communication standard such as Bluetooth (trade name) is used. However, the wireless interface is not limited thereto, and a wireless local area network (LAN) and a public mobile communication network may be used.

(2) Prediction Device (2-1) Hardware Configuration

Figure 3:
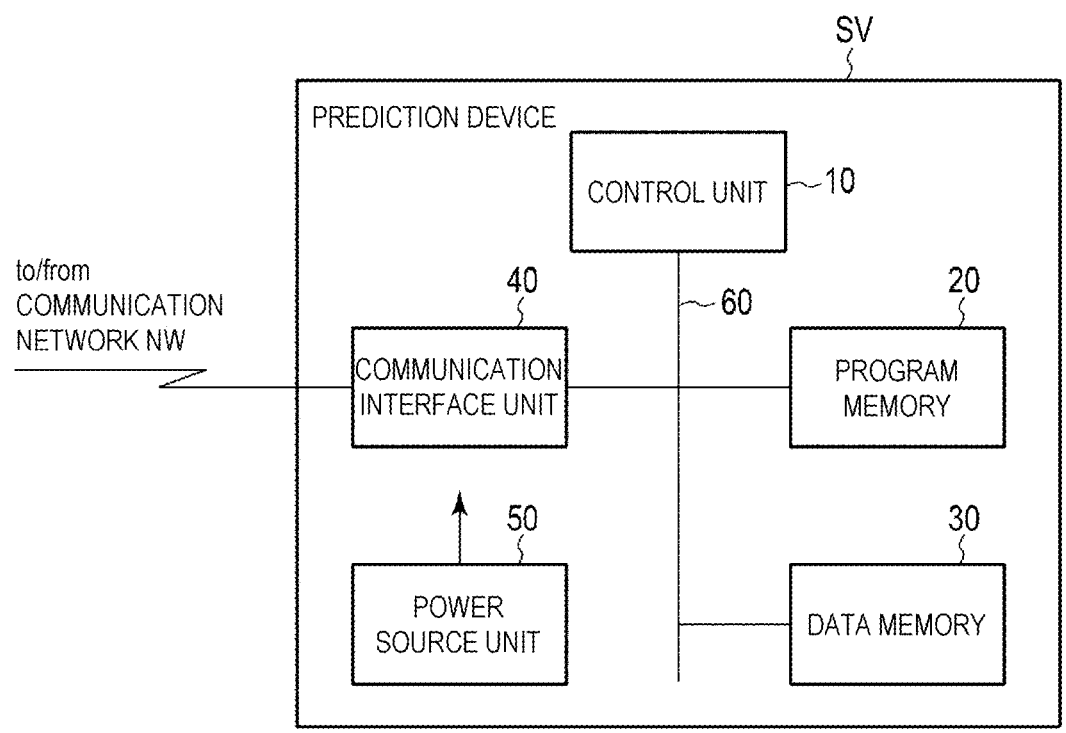
FIG. 3 is a block diagram illustrating the disease onset risk prediction device according to an embodiment of the present invention, particularly a hardware configuration of the prediction device.

For example, the prediction device SV is a server computer or a personal computer and is configured as described below. FIG. 3 is a block diagram illustrating the hardware configuration.

The prediction device SV includes a control unit using a hardware processor called a central processing unit (CPU) or the like, and a control unit 10 is connected to a program memory 20, a data memory 30, and a communication interface unit 40 via a bus 60. Note that the reference symbol 50 indicates a power source unit.

The program memory 20 is achieved by using a nonvolatile memory such as a hard disk drive (HDD), a solid state drive (SSD), and a ROM and stores a group of programs for achieving processing executed by the prediction device SV. The data memory 30 is achieved by using a volatile memory such as a DRAM or a nonvolatile memory such as an HDD and an SSD described above, which is capable of performing writing and reading as required and is used to store the biological information and the sleep information that are acquired from the measurement devices BT1 to BTn or to store the criteria. The communication interface unit 40 performs data communication between the doctor terminals DT1 to DTm and the information terminals IT1 to ITn via the communication network NW.

(2-2) Software Configuration

Figure 4:
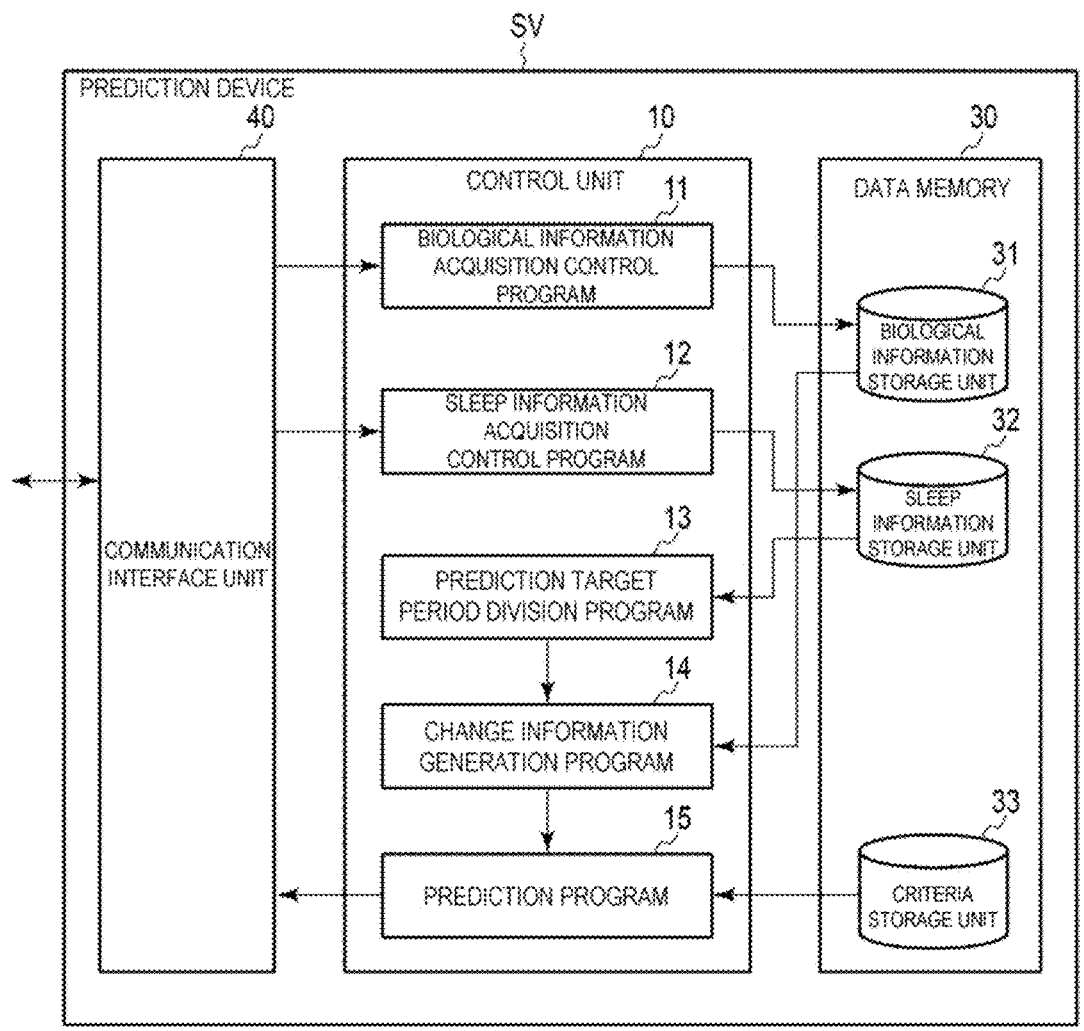
FIG. 4 is a block diagram illustrating the disease onset risk prediction device according to an embodiment of the present invention, particularly a configuration of software and data memory of the prediction device.

FIG. 4 is a block diagram illustrating a software configuration and a memory configuration of the prediction device SV.

The data memory 30 includes a biological information storage unit 31, a sleep information storage unit 32, and a criteria storage unit 33.

The biological information storage unit 31 is used to store the blood pressure data and the pulse wave determination data received from each of the information terminals IT1 to ITn of the users. The sleep information storage unit 32 is used to store the information indicating the sleep time period received from each of the information terminals IT1 to ITn of the users.

For example, the criteria storage unit 33 stores the criteria that is set in advance for determination of an onset risk for cardiovascular and cerebrovascular diseases. For example, the criteria are for determination of a degree of change in blood pressure values and in frequency of occurrence of irregular pulse waves during sleep stable time, with respect to early-morning hypertension and irregular pulse waves being onset factors for cardiovascular and cerebrovascular diseases.

As an example, according to a hypertension treatment guideline and the like, a case where a systolic blood pressure and a diastolic blood pressure that are measured at home in the morning are continuously 135 mmHg or more and 85 mmHg or more, respectively, is defined that early-morning hypertension is suspected. Further, a case where a systolic blood pressure within three hours after rising falls within a range of from 170 mmHg to 180 mmHg or more and where a blood pressure rise for three hours after and before rising falls within a range of from 30 mmHg to 50 mmHg is defined that early-morning hypertension is suspected. In view of this, in the embodiment, the criteria are set in accordance with the references defined in the hypertension treatment guideline and are stored in the criteria storage unit 33.

Meanwhile, the program memory 20 stores: a biological information acquisition control program 11, a sleep information acquisition control program 12, a prediction target period division program 13, a change information generation program 14, and a prediction program 15, and the control unit 10 achieves the processing in the embodiment by causing the CPU to execute each of the programs 11 to 15.

The biological information acquisition control program 11 executes processing in which the communication interface unit 40 receives the blood pressure data and the pulse wave determination data transmitted from each of the information terminals IT1 to ITn of the users; and in which the blood pressure data and the pulse wave determination data that are received are sorted for each user in order of the measurement time and are stored in the biological information storage unit 31, in accordance with the user ID and the measurement time that are added to or inserted in the data.

The sleep information acquisition control program 12 executes processing in which the communication interface unit 40 receives the information indicating the sleep time period or the information indicating the determination result of the sleep condition that is transmitted from each of the information terminals IT1 to ITn of the users; and in which the received information is associated with the user ID and is stored in the biological information storage unit 31.

The prediction target period division program 13 executes processing in which the sleep time period is set as the prediction target period for each user, based on, for example, the information indicating the sleep time period that is stored in the sleep information storage unit 32; in which the middle time in the sleep time period is set as a division boundary point; and in which the sleep time period is divided into a first half time period and a second half time period at the division boundary point.

The change information generation program 14 executes processing described below.

(1) Processing in which, for each of the users and each of the first half and the second half time periods in the sleep time period set by the prediction target period division program 13, the blood pressure data in which the time period includes the measurement time is read from the biological information storage unit 31 and an average value thereof is calculated; and in which a degree of change (ratio) in the average values in the first half time period and the second half time period is calculated. Note that calculation of the average value and the degree of change in the blood pressure data may be performed for each of a systolic blood pressure and a diastolic blood pressure or may be performed only for a systolic blood pressure.

(2) Processing in which, for each of the first half and the second half time periods in the sleep time period, the pulse wave determination data in which the time period includes the measurement time is read from the biological information storage unit 31 and the frequency of occurrence of irregular pulse waves is calculated; and in which a degree of change (ratio) in the frequency of occurrence in the first half time period and the second half time period is calculated.

(3) Processing in which a weight coefficient is added to synthesize the degree of change in the blood pressure data calculated in the processing (1) described above and the degree of change in the frequency of occurrence of irregular pulse waves calculated in the processing (2); and in which a score (also referred to as a total risk) indicating a degree of time change in the biological information obtained by totalizing the blood pressure and the frequency of occurrence of irregular pulse waves in the sleep time period is calculated. Note that the weighting and synthesizing processing uses addition, multiplication, or arithmetic processing of a combination of those.

The prediction program 15 executes processing described below.

(1) Processing in which the score calculated by the change information generation program 14 is compared with the criteria stored in the criteria storage unit 33; and in which the comparison result is regarded as prediction data of an onset risk for cardiovascular and cerebrovascular diseases.

(2) Processing in which, when the content of the prediction data of the onset risk indicates that "the onset risk is high", a notification message indicating the content is formed; and in which the notification message is transmitted, for example, through use of e-mail, from the communication interface unit 40 to the information terminals IT1 to ITn of the corresponding users or the terminals DT1 to DTm of family physicians of the corresponding users.

(3) Operation Examples

Next, one example of an operation of the system configured as described above is described.

(3-1) Operations of User Terminals UT1 to UTn

For example, the measurement devices BT1 to BTn measure blood pressure (including a systolic blood pressure and a diastolic blood pressure) and pulse waves of the users by operations by the users or at a timing or a time interval that is set in advance, and the blood pressure data and the pulse wave data that are measured are wirelessly transmitted to the information terminals IT1 to ITn. In this case, the measurement time and the user identification information (user ID) are added to or inserted in the blood pressure data and the pulse wave data. Note that, in this operation example, a case where blood pressure and pulse waves are measured automatically at an interval of one hour is described.

The information terminals IT1 to ITn receive the blood pressure data and the pulse wave data transmitted from the measurement devices BT1 to BTn and temporarily accumulate the data in a memory. Further, a deviation amount of each pulse wave from the original measurement timing is detected based on the pulse wave data. When the deviation amount is less than a predetermined amount, the pulse wave is determined as a regular pulse wave. When the deviation amount is a predetermined amount or more, the pulse wave is determined as an irregular pulse wave. For example, when a measurement timing of the pulse wave is deviated by 25% or more of the average measurement interval, the pulse wave is determined as an irregular pulse wave. In a case other than this case, the pulse wave is determined as a regular pulse wave. The regular/irregular determination data on this pulse wave (pulse wave determination data) is stored in the memory.

The information terminals IT1 to ITn read the blood pressure data and the pulse wave determination data accumulated in the memory for a fixed time, for example, and transmit the data to the prediction device SV via the communication network NW. Note that the blood pressure data and the pulse wave determination data may be transmitted from the information terminals IT1 to ITn and the prediction device SV every time when measurement is performed.

Further, the information terminals IT1 to ITn each generate information indicating sleep time of a user. The following two generation methods are conceivable.

(Method 1) Self-Declaration From User

A user manually inputs his or her sleep time period (bedtime and rising time) with his or her own terminal among the information terminals IT1 to ITn. The information terminals IT1 to ITn store the input information indicating the sleep time period in the memory, then read the information at a freely-selected timing after rising, and transmit the information as the sleep information to the prediction device SV. Note that, when the measurement devices BT1 to BTn each include an input unit, a user may input the sleep time period with the input unit of each of the measurement devices BT1 to BTn.

(Method 2) Estimation Form Pulse Wave Data

The information terminals IT1 to ITn each determine, based on the measured pulse wave data, a sleep condition of a user by the following methods, for example. FIGS. 9A to 9D are diagrams illustrating processing contents.

Figure 9A:
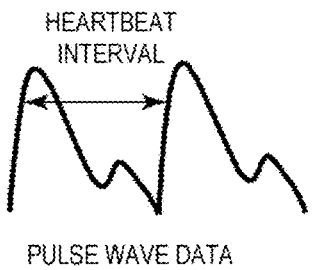
FIG. 9A is a diagram illustrating one example of pulse wave data.
Figure 9B:
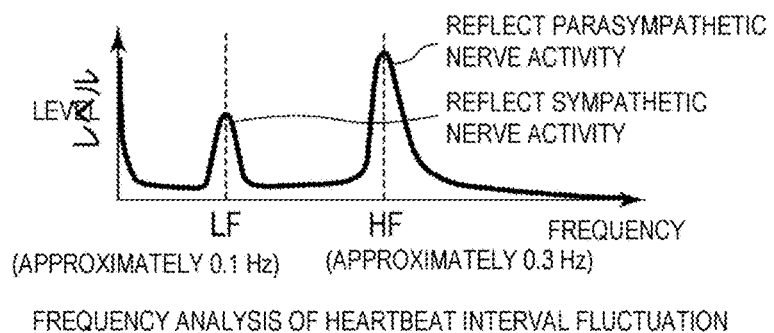
FIG. 9B is a diagram illustrating one example of frequency analysis results of heartbeat interval fluctuation.
Figure 9C:
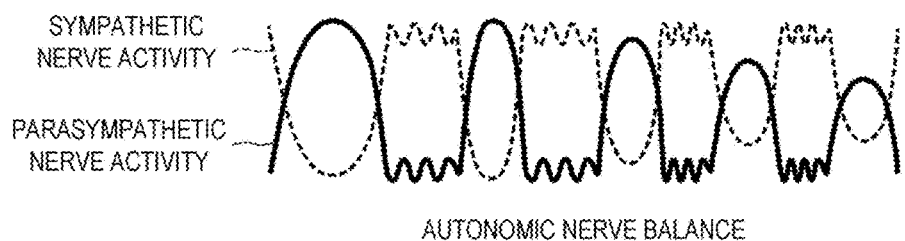
FIG. 9C is a diagram illustrating one example of change in autonomic nerve balance.

Specifically, first, a heartbeat interval (RRI) is detected from the pulse wave data (the wave form data shown in FIG. 9A). Subsequently, fluctuation components of the heartbeat interval are subjected to a frequency analysis. With this, as shown in FIG. 9B, a level of low frequency (LF) component of approximately 0.1 Hz, which is reflection of a sympathetic nerve activity; and a level of a high frequency (HF) component of approximately 0.3 Hz, which is reflection of a parasympathetic nerve activity are calculated. Further, autonomic nerve balance during sleep time as shown in FIG. 9C is calculated, based on the detection result of LF and HF.

Figure 9D:
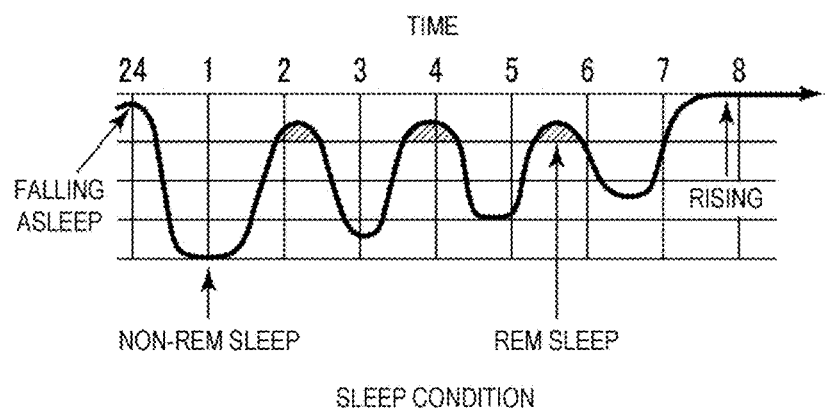
FIG. 9D is a diagram illustrating one example of temporal change in a sleep condition.

An autonomic nerve activity condition is known to have a certain correlation with depth and types of sleep (REM sleep and non-REM sleep). In general, when a parasympathetic nerve component is predominant, non-REM sleep takes precedence in many cases. When a sympathetic nerve component is predominant or pulse waves are disturbed, REM sleep takes precedence in many cases. In view of this, while focusing on this relationship, the information terminals IT1 to ITn associate autonomic nerve balance with a sleep condition as shown in FIG. 9D, for example.

Figure 10:
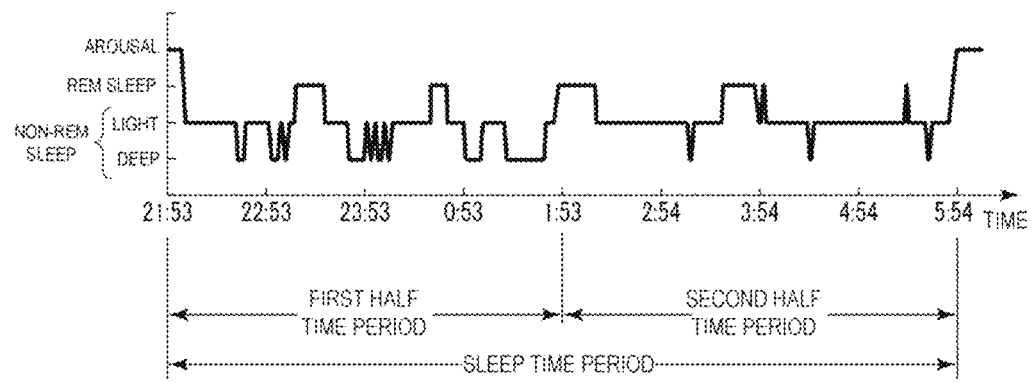
FIG. 10 is a diagram illustrating one example of sleep condition determination results.

More specifically, the information terminals IT1 to ITn define four sleep stages including REM sleep, deep non-REM sleep, light non-REM sleep, and arousal, for example, and associate the sleep condition with the four sleep stages, based on the calculation result of autonomic nerve balance. With this, for example, a determination result of the sleep condition shown in FIG. 10 is obtained. Note that discrimination between REM sleep and arousal can be determined more accurately in the following manner. For example, an acceleration sensor is provided to each of the measurement devices BT1 to BTn, the acceleration sensor detects body motion of a user, and arousal is determined when the body motion continues for a predetermined time or more.

The information terminals IT1 to ITn store the information indicating the determination result of the sleep condition in the memory, then read the information at a freely-selected timing after rising, and transmit the information as the sleep information to the prediction device SV.

Note that the determination method of a sleep condition described as (Method 2) given above is described in detail in "Evaluation of Sleep Quality and Sleep Monitoring System for Better Sleep", Kenichi KAMEYAMA, et al., Toshiba Review Vol. 61, No. 10, (2006), pp. 41-44.

(3-2) Operation of Prediction Device SV

Figure 5:
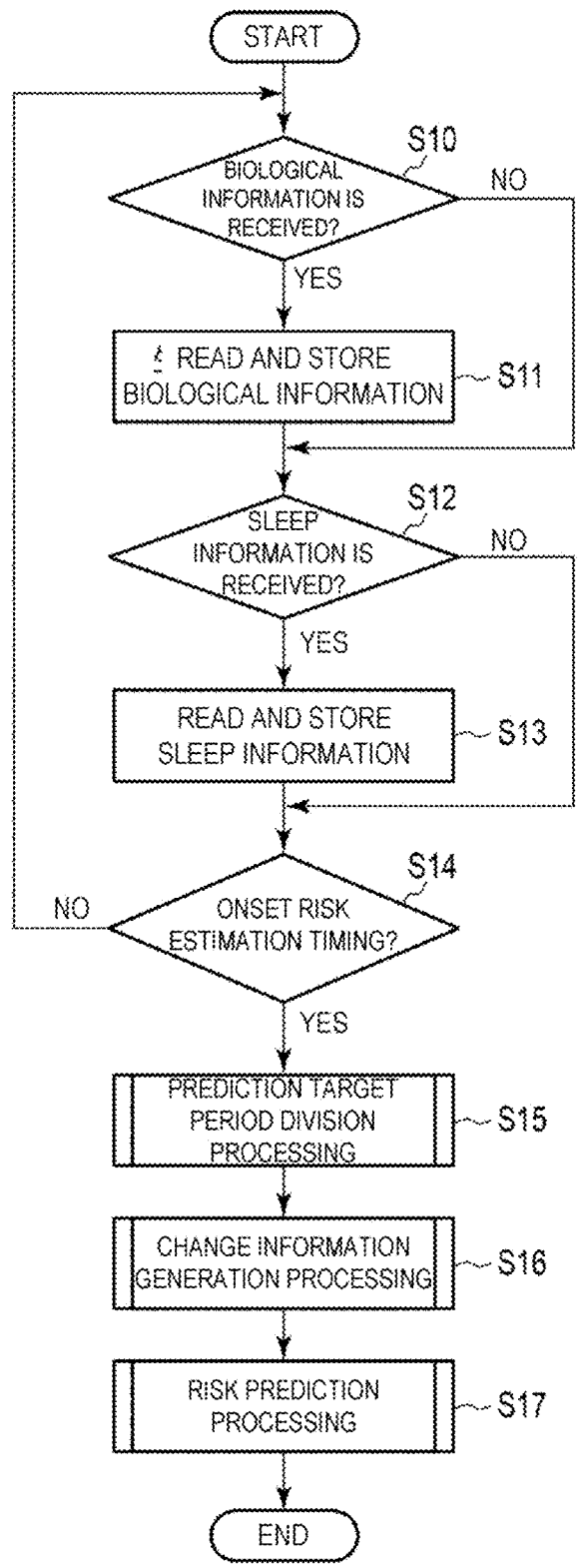
FIG. 5 is a flowchart illustrating a processing procedure and processing contents of disease onset prediction processing executed by the disease onset risk prediction device illustrated in FIG. 4.

The prediction device SV is operated as in the following. FIG. 5 is a flowchart illustrating a processing procedure and processing contents of the prediction device SV.

(3-2-1) Acquisition of Biological Information

The prediction device SV monitors reception of the biological information under control of the biological information acquisition control program 11 in Step S10. In this state, when the biological information, specifically, the blood pressure data and the pulse wave determination data are transmitted from the information terminals IT1 to ITn of the users, the blood pressure data and the pulse wave determination data are received by the communication interface unit 40, are taken in the control unit 10 in Step S11, and are stored in the biological information storage unit 31.

The processing of acquiring the blood pressure data and the pulse wave determination data described above is executed every time when the blood pressure data and the pulse wave determination data are newly transmitted from the information terminals IT1 to ITn. In this case, the blood pressure data and the pulse wave determination data are sorted for each user in accordance with the user ID and the measurement time that are added to or inserted in the data, are aligned in order of the measurement time, and are stored in the biological information storage unit 31.

(3-2-2) Acquisition of Sleep Information

The prediction device SV monitors reception of the sleep information under control of the sleep information acquisition control program 12 in Step S12. In this state, when the sleep information, specifically the information indicating the sleep time period or the information indicating the determination result of the sleep condition are is transmitted from the information terminals IT1 to ITn of the users, the information indicating the sleep time period or the information indicating the determination result of the sleep condition is received by the communication interface unit 40, is taken in the control unit 10 in Step S13, and is stored in the sleep information storage unit 32. Note that the sleep information transmitted from the information terminals IT1 to ITn is updated every day in some cases, and hence the received sleep information is stored in association with information indicating a date.

(3-2-3) Setting and Division of Predication Target Period

While executing the processing of acquiring the biological information and the processing of acquiring the sleep information, the prediction device SV monitors whether an onset risk estimation timing arrives in Step S14. For example, the onset risk estimation timing is set at an arousal timing of a user. The arousal timing is set, based on the acquired sleep information.

In this state, when the onset risk estimation timing arrives, first, the prediction device SV activates the prediction target period division program 13 in Step S15 and, under control of the prediction target period division program 13, executes prediction target period division processing in the following manner.

Figure 6:
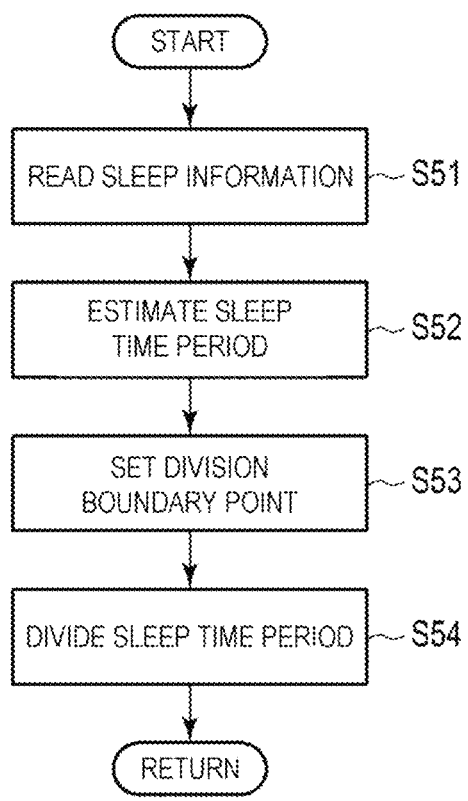
FIG. 6 is a flowchart illustrating a processing procedure and processing contents of estimation target period division processing in the disease onset prediction processing illustrated in FIG. 5.

FIG. 6 is a flowchart illustrating an example of a processing procedure and processing contents of the prediction target period division processing.

The prediction target period division program 13 first reads the sleep information on a corresponding date from the sleep information storage unit 32 in Step S151. Further, when the read sleep information is the information indicating the sleep time period, which is input by a user, in Step S152, the sleep time period is set as the prediction target period as is.

In contrast, when the estimation information is the information indicating the determination result of the sleep condition, which is generated from the pulse wave data, the prediction target period division program 13 estimates a sleep time period from the information and sets the estimated sleep time period as the prediction target period. For example, in the case of the information indicating the determination result of the sleep condition in FIG. 10, the sleep time period is estimated from a completion time point of an "arousal" state at the bedtime to a starting time point of an "arousal" state at the rising time.

Subsequently, in Step S153, the prediction target period division program 13 sets a division boundary point, based on the sleep time period set as the prediction target period. For example, the middle time of the sleep time period is set as the division boundary point as is. Alternatively, based on the information indicating the determination result of the sleep condition, a timing at which a state where "deep non-REM sleep" appears more frequently is shifted to a state where "deep non-REM sleep" appears less frequently is detected, and the timing is set as the division boundary point. For example, in FIG. 10, the frequency of the appearance of "deep non-REM sleep" is calculated at an interval of one hour, and a timing at which the calculation value is largely changed is set as the division boundary point.

Subsequently, in Step S154, the prediction target period division program 13 divides the sleep time period, which is set as the prediction target period in Step S152, into two time periods, through use of the division boundary point set in Step S154. For example, in the case of the sleep condition determination result shown in FIG. 10, a division into the first half time period and the second half time period is made at 1:53 AM.

(3-2-4) Generation of Change Information

The setting of the prediction target period and the division processing are completed. Subsequently, in Step S16, the prediction device SV activates the change information generation program 14 and, under control of the change information generation program 14, executes processing of generating change information on the biological information in the following manner.

Figure 7:
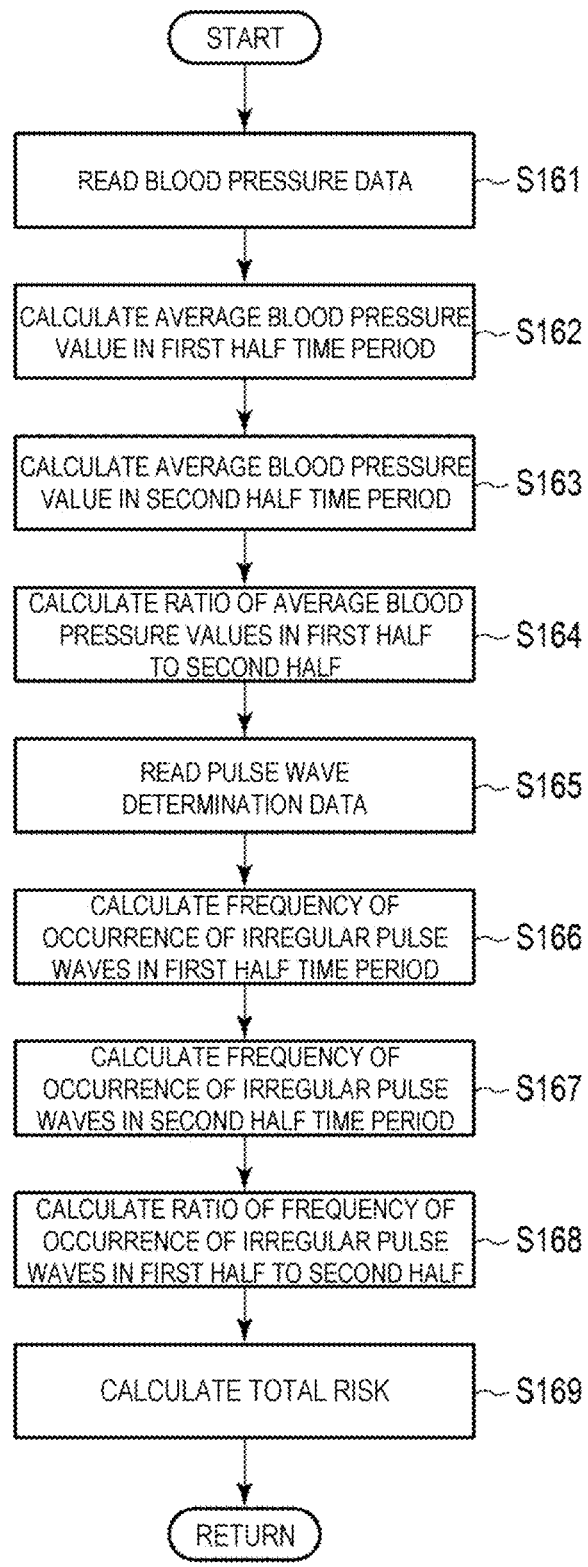
FIG. 7 is a flowchart illustrating a processing procedure and processing contents of change information generation processing in the disease onset prediction processing illustrated in FIG. 5.

FIG. 7 is a flowchart illustrating an example of a processing procedure and processing contents of the processing of generating change information on the biological information.

First, in Step S161, the change information generation program 14 reads, from the biological information storage unit 31, the blood pressure data in which the sleep time period set as the prediction target period includes the measurement time. In this case, reading of the blood pressure data may be performed separately in the first half time period and the second half time period in the sleep time period in advance.

The reading of the blood pressure data included in the sleep time period is completed. Subsequently, in Step S162, the change information generation program 14 calculates an average value of the blood pressure data of the read blood pressure data included in the first half time period. Further, along with this, in Step S163, an average value of the blood pressure data in the second half time period is calculated. The average value of the blood pressure data is calculated for each of a systolic blood pressure and a diastolic blood pressure.

Subsequently, in Step S164, the change information generation program 14 calculates a ratio of the calculated average value of the blood pressure data in the first half time period to the calculated average value of the blood pressure data in the second half time period.

Figure 11:
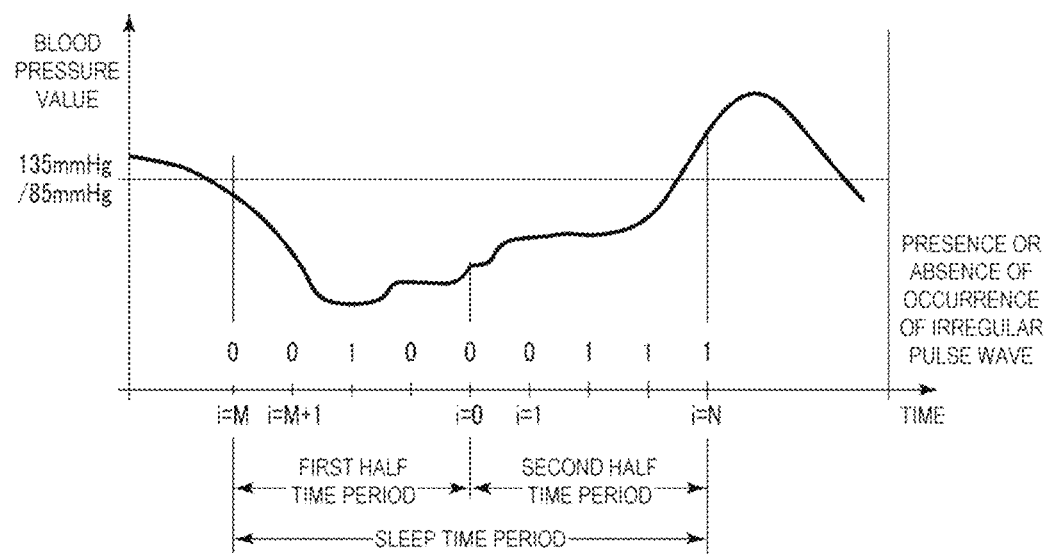
FIG. 11 is a diagram illustrating one example of change in blood pressure values in a sleep time period and presence or absence of the occurrence of irregular pulse waves.

For example, it is assumed that the current value of the blood pressure data in the sleep time period is as shown in BP of FIG. 11. In this case, the change information generation program 14 calculates a ratio riskbp of an average value of each of the blood pressure data bpi (i=M, M+1, . . . , −1) measured at measurement times i=M, M+1, . . . , −1 in the first half time period to an average value of each of the blood pressure data bpi (i=0, 1, . . . , N) measured at measurement times i=0, 1, . . . , N in the second half time period, through use of the following expression.

$$risk_{bp} = \frac{\sum_{i=0}^{N} \frac{bp_i}{N}}{\sum_{i=M}^{0} \frac{bp_i}{-M}}$$ [MATH. 1]

Subsequently, in Step S165, the change information generation program 14 reads, from the biological information storage unit 31, the pulse wave determination data in which the sleep time period set as the prediction target period includes the measurement time. In this case, similarly to the case of the blood pressure data, reading of the pulse wave determination data may be performed separately in the first half time period and the second half time period in the sleep time period in advance.

The reading of the pulse wave determination data included in the sleep time period is completed. Subsequently, in Step S166, the change information generation program 14 calculates an average value of the pulse wave determination data of the read pulse wave determination data included in the first half time period, specifically, the frequency of occurrence of irregular pulse waves. Further, along with this, in Step S167, an average value of the pulse wave determination data in the second half time period, specifically, the frequency of occurrence of irregular pulse waves is calculated.

Subsequently, in Step S168, the change information generation program 14 calculates a ratio of the calculated frequency of occurrence of irregular pulse waves in the first half time period to the calculated frequency of occurrence of irregular pulse waves in the second half time period.

For example, it is assumed that the current value of the pulse wave determination data in the sleep time period is "0" (regular pulse waves) or "1" (irregular pulse waves) as shown in FIG. 11. In this case, the change information generation program 14 calculates a ratio riskirh of the frequency of occurrence of irregular pulse waves based on each of the pulse wave determination data irhi (i=M, M+1, . . . , −1) measured and determined at the measurement times i=M, M+1, . . . , −1 in the first half time period to the frequency of occurrence of irregular pulse waves based on each of the pulse wave determination data irhi (i=0, 1, . . . , N) measured and determined at the measurement times i=0, 1, . . . , N in the second half time period, through use of the following expression.

$$risk_{irh} = \frac{\sum_{i=0}^{N} \frac{irh_i}{N}}{\sum_{i=M}^{0} \frac{irh_i}{-M}}$$ [MATH. 2]

Finally, in Step S169, the change information generation program 14 set the calculated ratio riskbp of the average values of the blood pressure data bpi in the first half time period and the second half time period in the sleep time period and the calculated ratio riskirh of the frequency of occurrence of irregular pulse waves in the first half time period and the second half time period in the sleep time period as weight coefficients W1 and W2, respectively, and multiplication is performed with the following expression.

$$risk = w1 \cdot risk_{bp} \times w2 \cdot risk_{irh}$$ [MATH. 3]

Further, the calculation result is output as change information (also referred to as total risk) risk, indicating a degree of time change in the biological information obtained by totalizing the blood pressure and the frequency of occurrence of irregular pulse waves.

Note that the weight coefficients W1 and W2 are set in advance in accordance with contribution ratios of blood pressure and irregular pulse waves with respect to early-morning hypertension, respectively. The weight coefficients W1 and W2 are set as appropriate in this manner, and thus determination accuracy for early-morning hypertension can further be improved.

(3-2-5) Determination of Onset Risk

The total risk risk is calculated. Subsequently, in Step S17, the prediction device SV activates the prediction program 15 and, under control of the prediction program 15, executes processing of determining an onset risk for cardiovascular and cerebrovascular diseases in the following manner.

Figure 8:
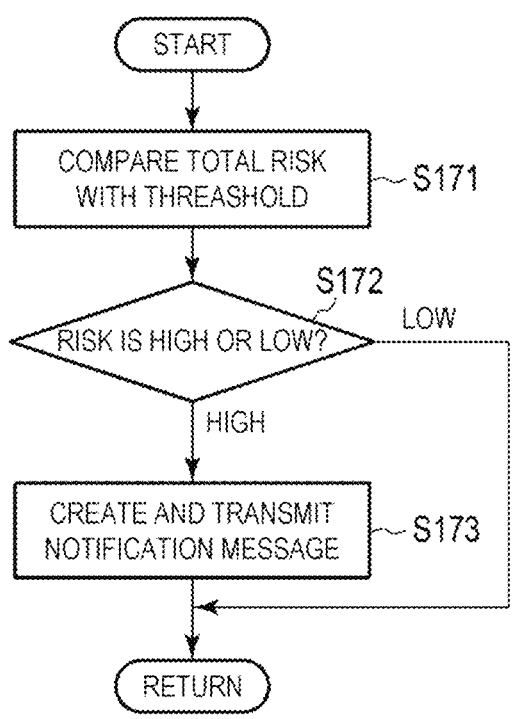
FIG. 8 is a processing procedure and processing contents of risk prediction processing in the disease onset prediction processing illustrated in FIG. 5.

FIG. 8 is a flowchart illustrating one example of a processing procedure and processing contents of the prediction program 15.

Specifically, in Step S171, the prediction program 15 reads, from the criteria storage unit 33, a determination threshold of an onset risk for cardiovascular and cerebrovascular diseases, which is set in advance by totalizing both early-morning hypertension and the frequency of occurrence of irregular pulse waves, and compares the total risk risk with the determination threshold. Further, in Step S172, it is determined that whether the total risk risk is higher or lower than the determination threshold.

As a result of the determination, when the total risk risk is higher than the determination threshold, in Step S173, the prediction program 15 forms a message for notifying a user that an onset risk for cardiovascular and cerebrovascular diseases is high and transmits the notification message from the communication interface unit 40 to the information terminal ITi of the corresponding user. Further, in this case, the notification message may include a message that intensive exercise should be avoided, in addition to that an onset risk for cardiovascular and cerebrovascular diseases is high.

Note that the prediction program 15 may transmit the notification message to the terminal DTi of a family physician of the corresponding user and may further transmit the message to information terminals used by people who are closely related to the user such as family members of the user or a manager at the office.

Actions and Effects

As described above, in the embodiment, the prediction device SV acquires, from each of the user terminals UT1 to UTn, the blood pressure data and the determination data on irregular pulse waves and also acquires the input data indicating the sleep time period or the information indicating the determination result of the sleep condition. Further, based on the input data indicating the sleep time period or the information indicating the determination result of the sleep condition, the sleep time period of the user is set as the prediction target period. After that, the sleep time period is divided into the first half and the second half, and the degree of change in the blood pressure data and the degree of change in frequency of occurrence of irregular pulse waves in each of the first half time period and the second half time period are calculated, are added with the weight coefficients, and are multiplied. With this, the score (the total risk) indicating a degree of time change in the biological information obtained by totalizing the blood pressure and the frequency of occurrence of irregular pulse waves in the sleep time period is calculated. Further, the total risk is compared with the determination threshold to determine whether an onset risk for cardiovascular and cerebrovascular diseases is high or low, and a user or the like is notified of the result.

Therefore, an early-morning hypertension state in which a blood pressure value abruptly rises in a time period before and after rising in the sleep time period can be detected by the processing method that is relatively simple. An onset risk for cardiovascular and cerebrovascular diseases is determined from the detection result, and the user can be notified of the result. Specifically, a short-term onset risk for cardiovascular and cerebrovascular diseases can be predicted every day. Thus, the user can avoid intensive exercise, bathing, and toilet activities after rising, for example. With this, the onset of cardiovascular and cerebrovascular diseases can be prevented.

Further, the sleep time period input by the user or the sleep time period estimated from the determination result of a sleep condition of the user is set as the prediction target period, and hence the accurate sleep time period can be set. With this, an onset risk for cardiovascular and cerebrovascular diseases due to early-morning hypertension can be predicted at high accuracy.

Further, when the division boundary point is estimated based on the determination data of the sleep condition and thus the sleep time period is divided into the first half and the second half, the sleep time period can be divided into the first half and the second half at an optimal timing. With this, accuracy of predicting an onset risk for cardiovascular and cerebrovascular diseases can further be improved. Meanwhile, when the middle time in the sleep time period is calculated and thus the sleep time period is divided into the first half and the second half at the middle time, setting of the division boundary point and processing of dividing the time period can be performed easily.

Modified Examples (1) In the embodiment, the case where the determination processing of regular/irregular pulse waves is executed by the information terminals IT1 to ITn is described as an example. However, the determination processing may be executed by the measurement devices BT1 to BTn or may be executed by the prediction device SV. When the determination processing is executed by the measurement devices BT1 to BTn, the measurement devices BT1 to BTn are not required to transmit pulse wave waveform data to the information terminals IT1 to ITn, and hence a communication data amount between the measurement devices BT1 to BTn and the information terminals IT1 to ITn can be reduced. Further, the determination processing is executed by the prediction device SV, and hence processing loads of the measurement devices BT1 to BTn and the information terminals IT1 to ITn can be reduced.

(2) In the embodiment, the case where the processing of analyzing the sleep condition from the pulse wave data is executed by the information terminals IT1 to ITn is described. However, the embodiment is not limited thereto. The information terminals IT1 to ITn may transmit the pulse wave data to the prediction device SV, the prediction device SV may determine the sleep condition based on the pulse wave data, the sleep time period may be estimated from the determination result, and the division boundary point may further be set. In this manner, processing loads of the information terminals IT1 to ITn can be reduced, and a service life of a battery can be prolonged.

(3) In the embodiment, the case where the sleep time period is divided into the first half and the second half is described. However, the embodiment is not limited thereto. For example, the sleep time period may be divided into three or more time periods, the average value of the blood pressure data and the frequency of occurrence of irregular pulse waves may be calculated for each of the time periods, and an onset risk for cardiovascular and cerebrovascular diseases may be predicted based on a degree of change in calculation values in the time periods. In this manner, for example, when a blood pressure surge is caused due to sleep apnea syndrome or the like in the middle time period in the sleep time period, such occurrence of the surge can be detected, and an onset risk for cardiovascular and cerebrovascular diseases can be predicted based on the degree.

(4) Further, the division boundary point in the sleep time period may not be set at the middle time in the sleep time period and may be set instead, for example, at a timing close to the rising time from the middle time. In this manner, even when a blood pressure surge is caused due to, for example, sleep apnea syndrome in the middle time period in the sleep time period, an onset of early-morning hypertension can be detected at high accuracy while reducing the influence of the surge.

(5) In the embodiment, the case where only one threshold is set as the criteria is described as an example. However, a plurality of thresholds may be set. When one threshold is given, it can be determined whether an onset risk for cardiovascular and cerebrovascular diseases is high or not. When a plurality of thresholds are given, it can be determined to what extent an onset risk for cardiovascular and cerebrovascular diseases is high. With this, a user can be notified of an appropriate message in accordance with an extent of an onset risk for cardiovascular and cerebrovascular diseases.

(6) In the embodiment, the case where the configuration of the prediction device SV is provided on a server computer on the Web or the cloud is described. However, the configuration of the prediction device SV may be provided in the information terminals IT1 to ITn that the users hold. Alternatively, when the measurement devices BT1 to BTn and the information terminals IT1 to ITn are formed as integrated devices such as wearable terminals, the configuration of the prediction device SV may be provided to the wearable terminals.

(7) In the embodiment, the blood pressure data and the pulse wave determination data are acquired as the biological information, and an onset risk for cardiovascular and cerebrovascular diseases is predicted through use of both the blood pressure data and the pulse wave determination data. However, the embodiment is not limited thereto. Only the blood pressure data may be acquired, and an onset risk for cardiovascular and cerebrovascular diseases may be predicted only through use of the blood pressure data. Further, when a disease, the symptom of which remarkably appears in time change in irregular pulse waves, is a prediction target, only the pulse wave determination data may be acquired to predict an onset risk for the disease.

(8) The embodiment of the present invention is described above in detail, but the description given above is merely an example of the present invention in every respect. It is needless to say that various changes and modification can be made without departing from the scope of the present invention. Thus, specific configurations in accordance with an embodiment may be adopted as appropriate at the time of carrying out the present invention.

Supplementary Notes

A part or the entirety of the embodiment can be described, as described in the following supplementary notes in addition to the scope of the claims, but the present invention is not limited thereto.

Supplementary Note 1

A disease onset risk prediction device including a hardware processor and a memory, the hardware processor executing acquiring and storing biological information of a user in the memory, the biological information being measured by a measurement unit, dividing a prediction target period into a plurality of time periods and generating information indicating change in the biological information in the plurality of time periods, and predicting an onset risk for a specified disease for the user by holding criteria being set in advance in accordance with the specified disease and comparing the information indicating change with the criteria.

Supplementary Note 2

A disease onset risk prediction method executed by a device including hardware processor and a memory, the hardware processor executing acquiring and storing biological information of a user in the memory, the biological information being measured by a measurement unit, dividing a prediction target period being set in advance into a plurality of time periods and calculating information indicating change in the biological information in the plurality of time periods, and predicting an onset risk for a specified disease for the user by storing, in the memory, criteria being set in advance in accordance with the specified disease and comparing the information indicating change with the criteria.

Supplementary Note 3

A disease onset risk prediction device, including: a biological information acquisition unit (1a, 11) configured to acquire biological information of a user, the biological information being measured by a measurement unit, a generation unit (1c, 14) configured to divide a prediction target period into a plurality of time periods and generate information indicating change in the biological information in the plurality of time periods, and a prediction unit (1d. 15) configured to predict an onset risk for a specified disease for the user by holding criteria being set in advance in accordance with the specified disease and comparing the information indicating change with the criteria.

REFERENCE SIGNS LIST

US User
1 Disease onset risk prediction device
2 Measurement device
1a Biological information acquisition unit
1b Biological information storage unit
1c Change information generation unit
1d Risk prediction unit
1e Criteria storage unit
SV Prediction device
UT1 to UTn User terminal
BT1 to BTn Measurement device
IT1 to ITn Information terminal
DT1 to DTm Doctor terminal
NW Communication network
10 Control unit
20 Program memory
30 Data memory
40 Communication interface unit
50 Power source unit
60 Bus
11 Biological information acquisition control program
12 Sleep information acquisition control program
13 Prediction target period division program
14 Change information generation program
15 Prediction program
31 Biological information storage unit
32 Sleep information storage unit
33 Criteria storage unit

The invention claimed is:

1. A disease onset risk prediction device, comprising:
a processor; and
a memory, wherein
the processor is configured to acquire biological information of a user, the biological information being measured by a measurement device,
the processor is configured to set a sleep time period of the user as a prediction target period, divide the prediction target period into a plurality of time periods, and generate information indicating change in the biological information in the plurality of time periods,
the processor is configured to predict an onset risk for a specified disease for the user by holding criteria being set in advance in accordance with the specified disease and comparing the information indicating change with the criteria,
the processor is configured to acquire information indicating a sleep condition of the user, the information being measured by the measurement device,
the processor is configured to estimate the sleep time period of the user and set the sleep time period as the prediction target period based on the information indicating the sleep condition, and
the processor is configured to set a division boundary point in the sleep time period based on the information indicating the sleep condition and to divide the sleep time period into a plurality of time periods at the division boundary point.

2. The disease onset risk prediction device according to claim 1, wherein
the processor is configured to acquire blood pressure information as the biological information,
the processor is configured to generate information indicating change in the blood pressure information being acquired in the plurality of time periods, and
the processor is configured to predict an onset risk for the specified disease for the user by holding a threshold being set in advance in accordance with the specified disease as the criteria and comparing the information indicating the change in the blood pressure information with the threshold.

3. The disease onset risk prediction device according to claim 2, wherein
the processor is configured to acquire information indicating a sleep time period of the user, the information being input with an input device,
the processor is configured to set the sleep time period of the user as the prediction target period based on the information indicating the sleep time period, and
the processor is configured to divide the sleep time period into a plurality of time periods.

4. The disease onset risk prediction device according to claim 2, wherein
the processor is configured to calculate statistic values of the biological information being measured at a plurality of times in each of the plurality of time periods and generate information indicating change in the statistic values being calculated in the plurality of time periods.

5. A non-transitory recording medium for storing a disease onset risk prediction program configured to cause the processor included in the disease onset risk prediction device according to claim 2 to acquire, set, divide, generate and predict.

6. The disease onset risk prediction device according to claim 1, wherein
the processor is configured to acquire blood pressure information and information indicating occurrence condition of irregular pulse waves as the biological information,
the processor is configured to generate first change information indicating change in the blood pressure information being acquired in the plurality of time periods,
the processor is configured to generate second change information indicating change in the information indicating occurrence condition of irregular pulse waves being acquired in the plurality of time periods,
the processor is configured to synthesize the first change information and the second change information by performing weighting with a coefficient being set in advance and to generate third change information indicating such a synthetic result as the information indicating change, and
the processor is configured to predict an onset risk for the specified disease for the user by holding a threshold being set in advance in accordance with the specified disease as the criteria and comparing the third change information with the threshold.

7. The disease onset risk prediction device according to claim 6, wherein
the processor is configured to acquire information indicating a sleep time period of the user, the information being input with an input device, the processor is configured to set the sleep time period of the user as the prediction target period based on the information indicating the sleep time period, and the processor is configured to divide the sleep time period into a plurality of time periods.

8. The disease onset risk prediction device according to claim 6, wherein the processor is configured to calculate statistic values of the biological information being measured at a plurality of times in each of the plurality of time periods and generate information indicating change in the statistic values being calculated in the plurality of time periods.

9. A non-transitory recording medium for storing a disease onset risk prediction program configured to cause the processor included in the disease onset risk prediction device according to claim 6 to acquire, set, divide, generate, predict and synthesize.

10. The disease onset risk prediction device according to claim 1, wherein the processor is configured to acquire information indicating a sleep time period of the user, the information being input with an input device, the processor is configured to set the sleep time period of the user as the prediction target period based on the information indicating the sleep time period, and the processor is configured to divide the sleep time period into a plurality of time periods.

11. The disease onset risk prediction device according to claim 10, wherein the processor is configured to calculate statistic values of the biological information being measured at a plurality of times in each of the plurality of time periods and generate information indicating change in the statistic values being calculated in the plurality of time periods.

12. A non-transitory recording medium for storing a disease onset risk prediction program configured to cause the processor included in the disease onset risk prediction device according to claim 10 to acquire, set, divide, generate and predict.

13. The disease onset risk prediction device according to claim 1, wherein the processor is configured to calculate statistic values of the biological information being measured at a plurality of times in each of the plurality of time periods and generate information indicating change in the statistic values being calculated in the plurality of time periods.

14. The disease onset risk prediction device according to claim 1, wherein the processor is configured to calculate statistic values of the biological information being measured at a plurality of times in each of the plurality of time periods and generate information indicating change in the statistic values being calculated in the plurality of time periods.

15. A non-transitory recording medium for storing a disease onset risk prediction program configured to cause the processor included in the disease onset risk prediction device according to claim 1 to acquire, set, divide, generate and predict.

16. A disease onset risk prediction method executed by a device including at least one hardware processor and a memory, the at least one hardware processor executing:

acquiring and storing biological information of a user in the memory, the biological information being measured by a measurement device;

setting a sleep time period of the user as a prediction target period, dividing the prediction target period being set in advance into a plurality of time periods, and calculating information indicating change in the biological information in the plurality of time periods; and predicting an onset risk for a specified disease for the user by holding criteria being set in advance in accordance with the specified disease and comparing the information indicating change with the criteria, acquiring information indicating a sleep condition of the user, the information being measured by the measurement device, estimating the sleep time period of the user and set the sleep time period as the prediction target period based on the information indicating the sleep condition, and setting a division boundary point in the sleep time period based on the information indicating the sleep condition and to divide the sleep time period into a plurality of time periods at the division boundary point.

* * * * *